(12) United States Patent
Agrawal et al.

(10) Patent No.: US 9,662,526 B2
(45) Date of Patent: May 30, 2017

(54) ACTIVE MOVEMENT TRAINING DEVICES, METHODS, AND SYSTEMS

(71) Applicant: The Trustees of Columbia University in the City of New York, New York, NY (US)

(72) Inventors: Sunil K. Agrawal, Newark, DE (US); Damiano Zanotto, New York, NY (US); Paul Stegall, Kansas City, MO (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 21 days.

(21) Appl. No.: 14/692,082

(22) Filed: Apr. 21, 2015

(65) Prior Publication Data

US 2015/0297934 A1 Oct. 22, 2015

Related U.S. Application Data

(60) Provisional application No. 61/982,237, filed on Apr. 21, 2014.

(51) Int. Cl.
*A63B 24/00* (2006.01)
*A63B 21/00* (2006.01)
(Continued)

(52) U.S. Cl.
CPC ........ *A63B 21/00181* (2013.01); *A61B 5/112* (2013.01); *A61B 5/22* (2013.01);
(Continued)

(58) Field of Classification Search
CPC ........ A63B 21/00181; A63B 21/00076; A63B 21/0058; A63B 21/023; A63B 21/4034;
(Continued)

(56) References Cited

U.S. PATENT DOCUMENTS 8,147,436 B2 4/2012 Agrawal et al.
8,608,674 B2 * 12/2013 Krebs ................. A61H 1/0218
601/24

(Continued)

OTHER PUBLICATIONS

"A step forward for stroke patients," *University of Delaware Messenger*, 17(1) [online], 2010 [retrieved on Aug. 18, 2014]. Retrieved from the Internet <URL: https://web.archive.org/web/20100529010240/http://www.udel.edu/udmessenger/vol17no1/stories/robotic_exoskeleton.html>.

(Continued)

*Primary Examiner* — Glenn Richman
(74) *Attorney, Agent, or Firm* — Potomac Law Group, PLLC; Mark Catan

(57) ABSTRACT

A rehabilitation machine can have a chassis with actuators positioned behind a patient area. The actuators can have supports projecting toward the patient area and can have respective adapters shaped to engage the legs of a patient at the thigh, the calf, and the foot while the patient is in a standing or walking posture. The actuators can also have motors, transition elements, and linkages connected to apply moments through the adapters to achieve, for each leg, hip adduction/abduction, hip flexion/extension, knee flexion/extension, and foot plantar flexion/dorsiflexion according to signals from a controller. The actuators can be confined to a space, largely behind the patient, such that free arm swing is permitted when the patient is attached.

25 Claims, 9 Drawing Sheets

(51) Int. Cl.
  A61B 5/11     (2006.01)
  A63B 22/02    (2006.01)
  G06F 19/00    (2011.01)
  A63B 69/00    (2006.01)
  A61B 5/00     (2006.01)
  A61B 5/22     (2006.01)
  A63B 23/00    (2006.01)
  A63B 21/005   (2006.01)
  A63B 21/02    (2006.01)
  A63B 71/06    (2006.01)
  A63B 22/00    (2006.01)

(52) U.S. Cl.
  CPC .......... *A61B 5/4848* (2013.01); *A61B 5/6823* (2013.01); *A61B 5/6828* (2013.01); *A61B 5/6829* (2013.01); *A61B 5/6835* (2013.01); *A63B 21/00076* (2013.01); *A63B 21/4009* (2015.10); *A63B 21/4015* (2015.10); *A63B 21/4025* (2015.10); *A63B 21/4034* (2015.10); *A63B 22/0235* (2013.01); *A63B 24/0087* (2013.01); *A63B 69/0064* (2013.01); *G06F 19/3481* (2013.01); *A61B 5/1121* (2013.01); *A61B 5/7246* (2013.01); *A61B 2505/09* (2013.01); *A61B 2562/0252* (2013.01); *A63B 21/0058* (2013.01); *A63B 21/023* (2013.01); *A63B 21/152* (2013.01); *A63B 21/4047* (2015.10); *A63B 22/0242* (2013.01); *A63B 2022/0094* (2013.01); *A63B 2023/003* (2013.01); *A63B 2024/0093* (2013.01); *A63B 2071/065* (2013.01); *A63B 2209/10* (2013.01); *A63B 2220/51* (2013.01); *A63B 2220/54* (2013.01)

(58) Field of Classification Search
  CPC ............ A63B 21/4015; A63B 21/4009; A63B 21/4025; A63B 21/4047; A63B 21/152; A63B 2023/003; A63B 5/112; A63B 5/6828; A63B 5/6829; A63B 5/6835; A63B 5/7246; A63B 5/1121; A63B 5/22; A63B 5/4848; A63B 5/6823; A63B 24/00; A63B 24/0062; A63B 24/0084
  See application file for complete search history.

(56) References Cited

U.S. PATENT DOCUMENTS

| | | | |
|---|---|---|---|
| 9,351,855 B2 * | 5/2016 | Swift | A61F 2/68 |
| 2008/0249438 A1 | 10/2008 | Agrawal et al. | |
| 2011/0245738 A1 | 10/2011 | Agrawal et al. | |
| 2014/0088729 A1 | 3/2014 | Herr et al. | |

OTHER PUBLICATIONS

Banala et al., "Robot assisted gait training with active leg exoskeleton (ALEX)," *IEEE Trans. Neural Syst. Rehabil. Eng.*, Feb. 2009, 17(1): pp. 2-8.

Bassett, Jonathan, "The Next Frontier," *Advance for Physical Therapy & Rehab Medicine*, Jul. 2012, 23(15): pp. 12-15, 30.

Krishnan et al., "A pilot study on the feasibility of robot-aided leg motor training to facilitate active participation," *Public Library of Science One (PLoS One)* [online], Oct. 2013 [retrieved on Aug. 8, 2014]. Retrieved from the Internet <URL: http://www.plosone.org/article/infor%3Adoi%2F10.1371%2Fjournal.pone.0077370>.

Lokomat® Pro. Brochure [online]. Hocoma AG [retrieved on Apr. 17, 2015]. Retrieved from the Internet <URL: http://www.hocoma.com/fileadmin/user/Dokumente/Lokomat/bro_LokomatPro_141008_en.pdf>.

Lokomat® Pro. Technical datasheet [online]. Hocoma AG [retrieved on Apr. 17, 2015]. Retrieved from the Internet <URL: http://www.hocoma.com/fileadmin/user/Dokumente/Lokomat/TECH_L6_140317_en.pdf>.

MARS Development Project D1, Executive Summary for "Cooperative Control Strategies for Robot-Aided Gait Therapy," *Rehabilitation Institute of Chicago* [online], [retrieved on Aug. 18, 2014]. Retrieved from the Internet <URL: http://www.ric.org/research/centers/mars3/Projects/development/d1-cooperative-control-strategies-for-robot-aided-gait-therapy/>.

Reiner et al., "Locomotor Training in Subjects with Sensori-Motor Deficits: An Overview of the Robotic Gait Orthosis Lokomat," *Journal of Healthcare Engineering*, 2010, 1(2): pp. 197-216.

Reinkensmeyer et al., "Tools for understanding and optimizing robotic gait training," *Journal of Rehabilitation Research & Development*, 2006, 43(5): pp. 657-670.

Roberts, Karen B., "Agrawal discusses role of robotic exoskeletons in stroke rehabilitation," *University of Delaware—UDaily*, Oct. 2010 [retrieved on Apr. 17, 2015]. Retrieved from the Internet: <URL: http://www.udel.edu/udaily/2011/oct/agrawal-robotic-exoskeletons102610.html>.

Stegall et al., "Rehabilitation Exoskeleton Design: Exploring the Effect of the Anterior Lunge Degree of Freedom," *IEEE Trans. on Robotics*, Apr. 2013, 29(4): pp. 838-846.

Van Asseldonk et al., "Robot-aided gait training with LOPES," *Neurorehabilitation Technology*, 2012, pp. 379-396.

Zanotto et al., "Adaptive assist-as-needed controller to improve gait symmetry in robot-assisted gait training," 2014 *IEEE International Conference on Robotics and Automation (ICRA)*, May 2014, pp. 724-729.

Zanotto et al., "Alex III: A Novel Robotic Platform with 12 DOFs for Human Gait Training," *2013 IEEE International Conference on Robotics and Automation (ICRA)*, May 2013, pp. 3914-3919.

* cited by examiner (a) Error area between the left and right footpath, normalized to the area of the right footpath (NEA).

(b) DS ratio (Right/Left) for each subject.

ACTIVE MOVEMENT TRAINING DEVICES, METHODS, AND SYSTEMS

CROSS-REFERENCE TO RELATED APPLICATIONS

The present application claims priority to U.S. Provisional Application No. 61/982,237, entitled "ACTIVE MOVEMENT TRAINING DEVICES METHODS AND SYSTEMS" filed Apr. 21, 2014, which is hereby incorporated herein by reference in its entirety.

STATEMENT REGARDING FEDERALLY SPONSORED RESEARCH OR DEVELOPMENT

This invention was made with government support under HD38582 awarded by the National Institutes of Health (NIH). The government has certain rights in the invention.

BACKGROUND

With an aging population comes the increased need for improved rehabilitation technologies for disabilities caused by brain and spinal cord injury, stroke and other neurological and orthopedic conditions. For stroke victims, intense physiotherapy is often required to regain and improve ambulatory and brain functions. As the population ages, the need for rehabilitation therapy has increased dramatically. Patients suffering from brain and spinal cord injury, stroke or other neurological and orthopedic conditions may benefit from mobility assistance and therapeutic devices. Current attempts at gait therapy improve function, but are labor intensive and limited by the demands and availability of physical therapists. The success of treatment is limited by the physical demands and availability of physical therapists. Robotic devices have been proposed for gait rehabilitation and can potentially reduce the physical burden on healthcare providers and the financial burden on patients.

SUMMARY

The disclosed subject matter includes a treadmill-based bilateral exoskeleton for gait therapy applications that can simultaneously apply controlled forces to the pelvis, knee and ankle joints. In embodiments, the technology provides twelve total degrees of freedom in the pelvis and legs to facilitate symmetric recovery and expand available therapeutic training regimens for gait therapy. Disclosed technology may also be used to evaluate/track gait, motor control and recovery of function. In embodiments, the technology includes a robotic walking assist device comprised of a bilateral exoskeleton that applies controlled forces to the pelvis, hip, knee and ankle joints simultaneously. In embodiments, the technology includes a treadmill-based exoskeleton that can allow for quantitative assessment of progress and improved recovery.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DESCRIPTION

A gait training machine is capable of applying a wide range of forces on a patient during treadmill gait-training, while allowing for natural movements of the walking subject when corrective forces are not required. Four degrees of freedom (DOFs) are activated at the pelvis and four DOFs are activated for each leg. Control of the machine permits three operating behaviors and a selectable range in-between:

1. transparent mode (zero-interaction) where the machine overcomes friction, weight, and inertia forces to permit freedom of natural movement;
2. assistive/resistive mode (variable interaction) where the machine applies forces to guide the patient's movements toward a target path but does not force the patient through the path beyond a certain force limit, which may be dependent on the phase of the cyclical path; and
3. locked mode (infinite stiffness) where the machine prevents any deviation from the target path of movement.

The controller scheme may be an impedance controller, making it, effectively, a haptic interface running an impedance controller. The machine may reproduce any level of impedance between its limits. Practical requirements limit the limits due to actuator saturation and controller bandwidth. Compensating the mechanical impedance of the device (friction, gravity and inertial contributions sensed at the movement training apparatus/subject interfaces) is imperfect due to limitations of acceleration estimation. To minimize the demand on such active compensation, the machine is configured to minimize inertia including features such as moving heavy parts of actuators to a stationary frame or as close as possible to a fixed base and then using flexible transmissions (e.g., cables and timing belts) to transmit power to the distal links. This has the additional advantage of allowing powerful actuators. Components such as adapters for the patient are as light as practical.

The machine also permits other factors that make the aided gait of the user as realistic as possible. The machine's designs, according to embodiments, permit full and natural arm swing. All components that may interfere with arm swing are positioned out of the way. In addition, the bottom of the foot may be unobstructed and the patient's weight may be supported in a normal fashion through the legs with pressure on the bottoms of the feet. The machine also provides features to avoid visual obstruction by locating major components out of view of a connected user.

Figure 3:
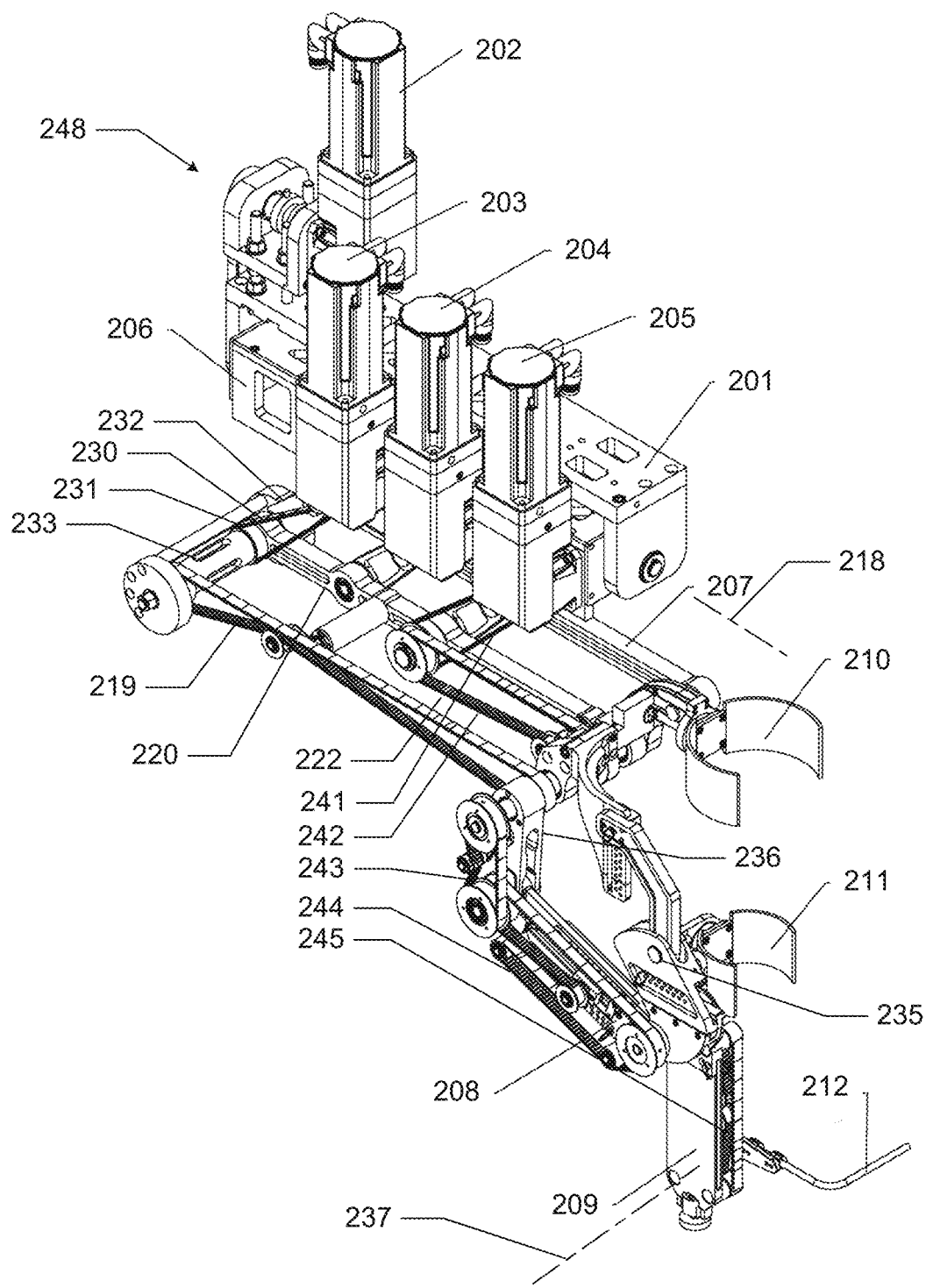
FIG. 3 is an oblique view of a prototype leg actuator, tested experimentally, according to embodiments of the disclosed subject matter.
Figure 4:
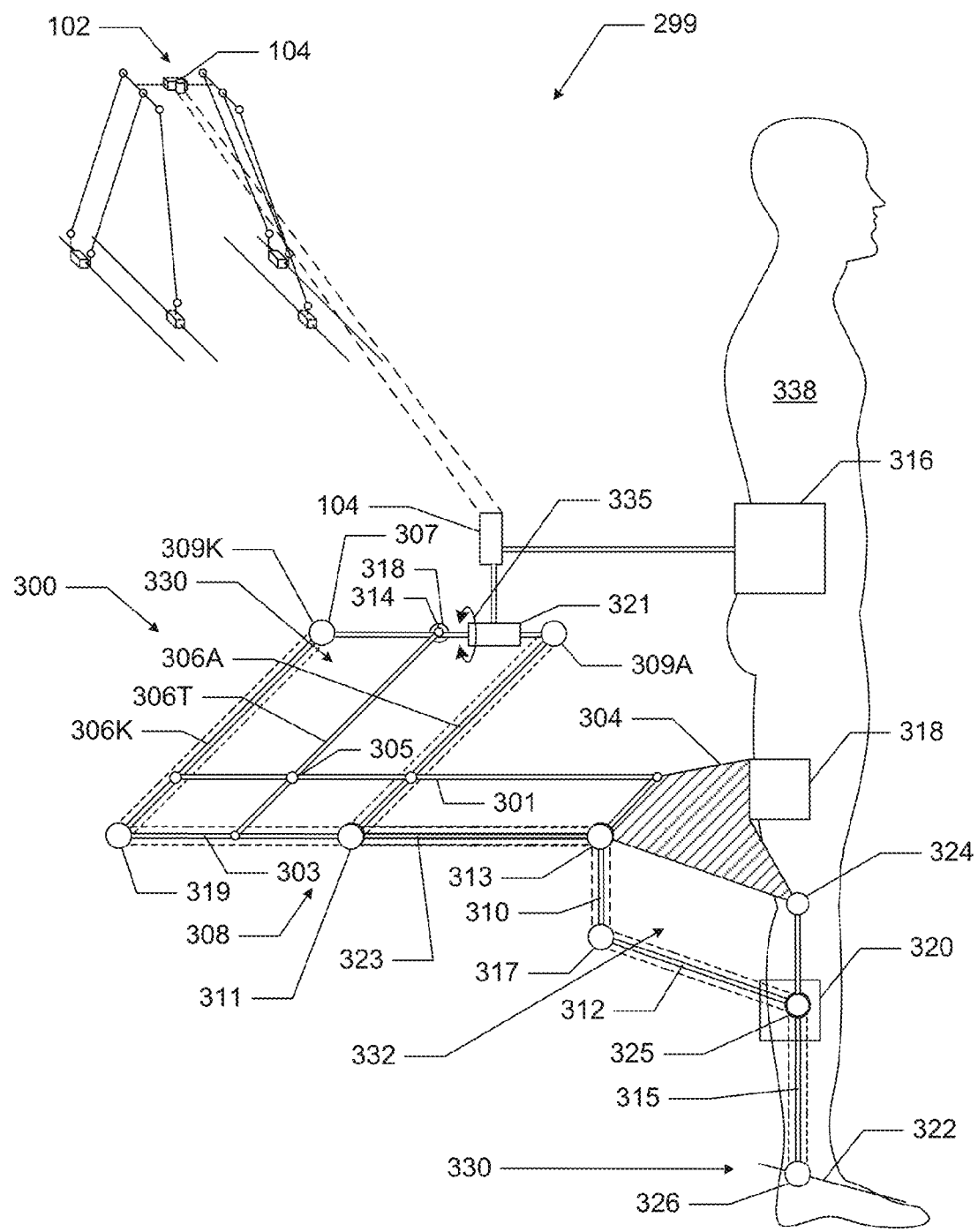
FIG. 4 shows the linkages that form the leg actuator of the device of FIG. 3 and the related adapters that interface to a patient, according to embodiments of the disclosed subject matter.

Referring to FIGS. 3 and 4, a main support plate 201 is attached to a trolley platform 102 (described with reference to FIG. 1) and supports the weight of the adduction/abduction box 206. The hip adduction/abduction box 206 can rotate with respect to the former by means of a timing-belt transmission actuated by the hip adduction/abduction motor 202 through a gearbox 248. The hip adduction/abduction axis passes through the hip and is parallel to the line shown at 218. Knee motor 203, hip motor 204, and ankle motor 205 are attached to the adduction/abduction box 206 and actuate the 3 DOFs which control flexion/extension of the hip and knee joints and plantar/dorsiflexion of the ankle. An output of the hip motor 203 drives a hip parallelogram linkage 207 which has a virtual pivot axis through the hip and controls the rotation of the thigh adapter 210 in the hip and knee flexion/extension plane (parasagittal plane). The knee motor 203 controls the rotation of the knee adapter 211 about a knee flexion/extension axis 235 that coincides with a virtual knee pivot axis of an attached patient. An output shaft of the knee motor 203 is connected through a gearbox to drive a pulley 231 through a belt 230, while the left-most member 232 of the hip parallelogram linkage 207 can freely rotate about the shaft 233. The driving pulley controls the rotation of a crank 236 that forms a left-most link of a knee parallelogram linkage 208 by means of pulleys through two belt loops 230, 219, each positioned by fixed-length links 220, 232. This arrangement decouples the rotation of the knee in the hip and knee flexion/extension plane from that of the hip in the same plane. The knee parallelogram linkage 208 includes a shank link 209 as a driven member of the parallelogram 208. The shank adapter 211 is rigidly attached to the shank link 209, though their relative positions can be adjusted manually.

The ankle motor 205 controls the rotation of an ankle lever 212 about an ankle plantar/dorsiflexion axis 237 independently of the other DOFs that are driven in the same plane. As in the case of the shank adapter, the ankle lever position relative to the shank link is controlled through a driven pulley through drive belts by the ankle motor. An output pulley is driven by five belt loops 241-245 with the loop 245 being within the shank link 209. The ankle 212 lever is rigidly attached to the output pulley, and includes an L-shaped rod that may be covered with foam wrap. The device is designed to apply plantar-flexion torque by pushing the midfoot from the top, thus preserving the sensed ground reaction forces (which, ideally, would be the same as those in normal walking). Dorsiflexion is achieved by means of adjustable webbing connected to the rod 212 which lifts the foot.

Manual adjustments may be used to facilitate alignments between human and movement training apparatus joints and accommodate different thigh and shank lengths. In embodiments, the spacing between joints can be adjusted through lead screws driven by a separate hand-held drive to make rapid changes between patients. Alternatively, a cable drive could be used to couple a lead screw to a motor drive that is automatically controlled by the system controller. The cable drive would avoid complexity and weight in the system. For drives requiring low backlash, a chain of drive tubes with beam or bellows drives may provide torque rigidity with high flexibility. Passive spring tensioners may be used in adjustable links carrying pulleys to produce the pretensions in the belts running through the links.

Mechanical end-stops and switches may be provided to prevent the range of motion for any joint from exceeding one expected for a patient. Automatic adjustment of the limit switches may be provided through a controller and positioning actuator. In addition, or alternatively, the controller may be programmed to limit the range ("Software bumper-stops") according to the patient. In embodiments, force and/or torque sensors connected to the adapters can output signals to the controller which may interpret them in conjunction with other adapter force and/or torque sensor inputs to recognize out of bound conditions such as over-extension of a single joint. Force and/or torque sensor inputs may be transient inputs and their time-based behavior may be characterized to form multiple inputs based on statistics, components of orthogonal base sets, etc. A safe configuration space can be defined using various techniques that can probabilistically classify large (many variable) state vectors. The data model may be stored in the controller and different models may be stored for different individual patients or different classes of patients.

Figure 1:
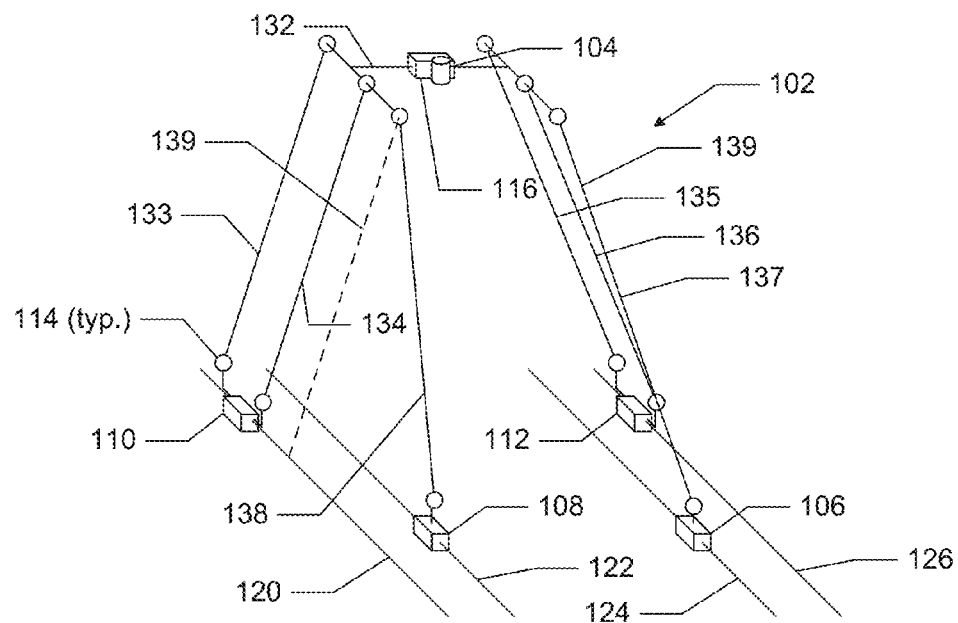
FIG. 1 shows, schematically, a kinematic primary actuator structure for supporting leg actuators and for actuating a lower back adapter, thereby providing translational and rotational assisted motion or resistance to a walking patient, according to embodiments of the disclosed subject matter.
Figure 2:
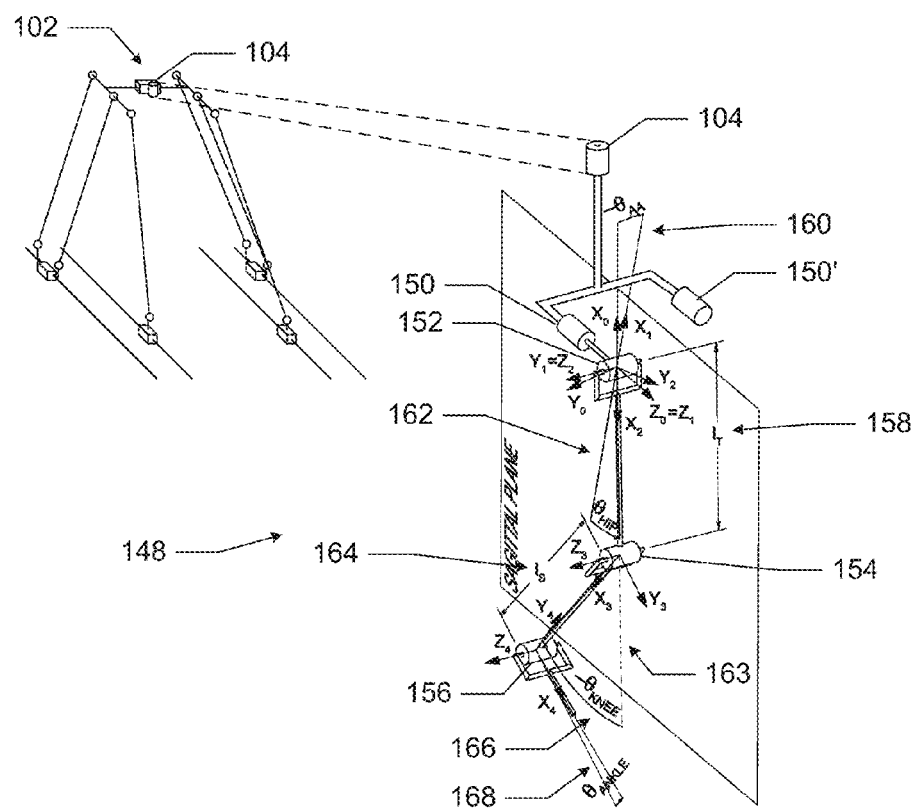
FIG. 2 shows a kinematic equivalent of a leg actuator with four degrees of freedom, according to embodiments of the disclosed subject matter.

The leg actuator interacts with the human leg at three interfaces: the thigh adapter, the shank adapter and the ankle lever. The hips have one interface with three DOFs. FIGS. 1, 2, and 4 will now be referenced to elaborate further the kinematics of the principal embodiments. FIG. 1 shows the trolley platform 102 that provides four degrees of freedom for the hips and support for a platform 132 that in turn connects the leg actuators through a revolute joint 104, thereby permitting rotation of the hips and the leg actuators about the vertical axis. A combination of the rotation of the revolute joint 104 with translation can produce rotation about the vertical axis through the hips of the patient. Translation is supplied through a prismatic joint 116, to which the revolute joint is attached, which rides along a link 132 driven by a suitable linear driver. The link 132 provides a platform that joins Cardan universal joints 114 at ends of vertical leg links. Rear leg links 133, 134 and 135, 136 support vertical and anterior/posterior motions of the support platform. The leg links 133, 134 and 135, 136 define a pair of parallel linkages, with Cardan universal joints 114 at the top and the bottom. Due to the nature of the parallel linkages, the combination of rear legs form virtual legs 139 (one of which is hidden behind front leg 137) that run parallel to the rear legs 133, 135 and pass through the top of a respective front leg 138, 137.

The rear leg links 133, 134 and 135, 136 connect to rails 120, 126 through prismatic links 110, 112 and respective universal joints 114. The front leg links 137, 138 connect to rails 122, 124 through prismatic links 108, 106 and respective universal joints 114. The rear prismatic joints 110, 112 ride on rear rails 120, 126 and the front prismatic joints 106, 108 ride on front rails 122, 124. Without interconnection, the top of the each leg 133, 134, 135, 136, 137, and 138 is independently capable of reaching a spherical shell. As a parallelogram linkage system, legs 133 and 134, as well as virtual leg 139, can also reach a spherical shell independently of front leg 138. By connecting the top of the front and virtual legs together—as it is done on the left and right sides of the platform—the reachable space is restricted to the intersection of the front and virtual legs' shells, i.e. a common circle defined by rotating the tip of the triangle formed the front leg the virtual leg and a line joining the bases thereof around that base as an axis. The circle lies in the radical plane of the two spheres, with its center lying on the axis that connects the bases of the two legs (axis of rotation in FIG. 1), and its radius being the height of the triangle formed by the same axis and the two legs. The left and right sides of the platform are connected to each other with rails. If the radical planes of both sides were the same, then the structure would behave like a four bar linkage in that plane. However, as shown, the front prismatic joints 106, 108 (and rails 122, 124) are closer together than rear prismatic joints 110, 112 (and rails 120, 126). Thus, distinct radical planes are created, thereby fixing the structure for any given position of the lower prismatic joints. Moving all the lower prismatic joints 106, 108, 110, 112 forward or backwards creates anterior and posterior motion, respectively. Increasing or decreasing the distance between the front and rear pairs of prismatic joints 106, 108 and 110, 112 produces inferior and superior motion, respectively. On the platform link 132 connecting the left and right side leg sets rides the prismatic joint 116 that produces lateral motion of the pelvis adapter and leg actuators by driving the prismatic joint 116. The exoskeletal legs and the pelvic adapter are attached after revolute joint 104. Pivoting about the revolute joint is driven by a separate motor. Since the revolute joint 104 is the center of rotation of the leg actuators, support may be provided by a thrust bearing for stability and strength.

In an alternative embodiment, two planar PRRRP kinematic chains can be used. These are quadrilateral linkages with driven stages defining a variable and movable base. However, such a linkage requires lateral support which the present design provides by triangulation in the projection to the lateral plane, thereby allowing the use of universal joints. Universal joints can have a significant advantage. The moment arm created by the length of the support legs is high. If the moment had to be resisted by a revolute joint any lateral loading at the top of the support system would result in an extremely large moment at the base of each support leg. Conversely, by using universal joints, the ends of the support legs only see moments about the longitudinal axis of the leg, so they act mainly in compression. This allows for the use of smaller components, reducing mass and moment of inertia. The support legs themselves are angled inward to help take lateral loading and increase stability.

FIG. 2 shows an equivalent virtual mechanism embodied in each leg actuator. The leg actuators are supported by the revolute joint 104 which supports a leg actuator for each leg. Each leg actuator includes a revolute joint 150, 150' supporting rotation 160 in the coronal plane for abduction/adduction motion of the leg that may have an angular range of −15, 15 as indicated at 160. Rotation for Hip flexion/extension 162 in the parasagittal plane is supported by revolute joint 152 that may have an angular range of −30, 15 as indicated at 162. Rotation for knee flexion/extension 163 the parasagittal plane is supported by revolute joint 156 that may have an angular range of −70, 5 as indicated at 163. Rotation for ankle plantar/dorsiflexion 163 the parasagittal plane is supported by ankle revolute joint 156 that may have an angular range of −30, 20 as indicated at 158. Two leg actuator sets are supported, one at 150 and one at 150', although the left leg actuators are not shown past the revolute joint 150, 150'. Links between the joints 152 and 154 and between the joints 154 and 156 may be adjustable. In embodiments, adjustment is performed by loosening screws and shifting a link member through a slot and tightening. In further embodiments, the adjustments can be performed programmatically using a motor drive through a cable drive, multilink drive shafts such as constant velocity (e.g., Rzeppa six-ball CV joint or simple universal joint), Thompson coupling, helical (beam) coupling, bellows couplings, Cardan joint (double Cardan joint), or similar flexible couplings. The motors and gearing for such drives may be located on a fixed platform behind or otherwise remote from the patient.

In embodiments, the kinematic mechanism for the legs 148 is at least partially projected to the actual position of the patient's leg from a leg actuator linkage mechanism behind. In embodiments, the hip adduction/abduction revolute joint 150 is projected directly from behind the patient by a rotating member. In embodiments, the hip flexion revolute joint 152 is projected from a position behind the patient by a first parallelogram linkage system. In embodiments, the parallelogram linkage system rotates with support by the hip adduction/abduction revolute joint 150. In embodiments, the parallelogram linkage system carries a second parallelogram linkage that is carried by the first parallel linkage system and is positioned, at least partly behind the knee of the patient, and projects the knee revolute joint 154. In embodiments, the ankle revolute joint 156 is projected by a revolute linkage from a position adjacent the ankle through an axis perpendicular to the sagittal plane and supported and carried by the second parallel linkage mechanism generating the knee revolute joint 154. In embodiments, the drive forces for the knee and ankle are transmitted through belt drives supported by pulleys whose axes pass through revolute joints of the first parallelogram linkage three respective revolute joints of the second parallelogram linkage to a pulley whose axis passes through the revolute joint supporting the ankle flexion/dorsiflexion motion. The use of belt drive (in embodiments, timing-belt drives that have teeth) can provide light weight for low inertia. In embodiments, all the mechanisms for the leg are powered by motors that are supported on the joint supporting hip adduction/abduction revolute joint.

In further variations of the embodiments, the motors may be supported on a fixed platform and connected for driving the mechanisms by flexible drives rather than supporting the motors on the link 132 supported by the support mechanism 102 which in turn carries both leg actuators and pelvic adapter 210. The mass of elements carried by the platform 102 generates inertial resistance to vertical and horizontal motion of the pelvic adapter. In addition, the mass of the leg actuators coupled after revolute joint 104 generates a moment of inertia that must be overcome to generate rotation of the hips of the patient through the pelvic adapter. It will be noted that there are ten motors and transmissions (together, "drives") carried by the platform 102 link 132, four for each leg, one for hip lateral translation and one for hip rotation. These motors may be supported off the platform 132 on a stationary frame with flexible transmissions shafts coupling the mechanisms driven by them to the reduced output of these drives. In this way the inertia felt by a patient through the hips due to imperfect control response may be substantially reduced.

In further embodiments, three degrees of freedom may be created to support the ankle to provide, thereby, providing pronation/supination and internal and external rotation (rotation about the axis of the shank). In embodiments, only one of these additional DOFs is provided. In embodiments, the providing pronation/supination and internal and external rotation may be driven through belt and shaft drives respectively that follow the path of the ankle motion drive illustrated with respect to the embodiment of FIG. 3, for example and as further explained with reference to FIG. 4, below.

FIG. 4 illustrates aspects of the kinematic design of a leg actuator 300 which follows the basic design of the embodiment of FIG. 3 and others that are similar to it. Two leg actuators as at 300 are supported on a trolley platform 102 as described above. A single leg actuator is now described. A leg actuator is indicated at 300 but it is noted that two are attached to the trolley platform 102. A double parallelogram mechanism 330 has three diagonal links: a knee link 306K, a thigh link 306T, and an ankle link 306A that are coupled by horizontal links 301 and 303 and by revolute joints, which have been indicated as circles in the drawing, e.g., indicated at 305 but similarly for other smaller circles as should clear from the full description. The larger circles as at 309A, 309K, or 319 indicate a timing belt pulley or chain sprocket or similar mechanism. Some links as at 306K and 303 carry the belt, and these are illustrated by links with dotted lines. Some of the pulleys are driven by drives indicated by the larger circles such as those indicated by numerals 309A, 309K, which represent knee and ankle drives. Torque is applied to the thigh link 306T by a drive 318 thereby causing the double parallelogram mechanism 330 to pivot to drive the thigh of a patient 338 attached to thigh adapter 318 in an arc centered on the hip joint. This is accomplished by the double parallelogram mechanism 330 which projects the motion forwardly such that a virtual link between the hip and a position forward of the thigh adapter 318 (within the thigh itself) is generated. Element 304 which is shaded indicates a rigid structure which may be embodied in a set of links or other suitable configuration.

The knee of the patient 338 is moved relative to the thigh by a knee parallelogram mechanism 332. Two of the links 310, 312 of the knee parallelogram mechanism 332 carry timing belts which support the driving of plantar/dorsiflexion of the ankle. Torque is applied by a drive at 309K through a chain of timing belts to pulley 313 which is attached to link 317 which moves the knee parallelogram mechanism 332. Force is applied by the knee parallelogram mechanism 332 to the knee adapter 320. The motive force generated by the ankle drive 309A is transmitted through a chain of timing belts following timing belts supported over a course of links 306A, 323, 310, 312, 315 finally to apply torque to the ankle revolute joint 326. The torque is projected laterally from the side of the ankle through an axis that is centered on an effective axis or plantar/dorsiflexion of the ankle of the patient 338.

In any of the embodiments, each of the interfaces to the patient, for example including pelvic adapter 316, knee adapter 318, shank adapter 320, and ankle adapter 322 may be connected upstream to their driving effecters through a respective force and/or torque sensor (not shown). The force and/or torque sensors may provide independent signals for six DOFs. These sensors, as discussed below, may allow the controller to compensate for friction, weight, inertia, and other forces as well as enable feedback control.

Hip abduction/adduction is driven by a drive and supported on a revolute joint which are collectively indicated at 321. The motion follows the same motion as the hip and is around an axis that intersects with an attached patient 338. Thus this motion is also projected from a mechanism located behind the patient 338 and mechanically generates a virtual axis (as opposed to doing so programmatically as is the case with rotation about the vertical axis of the body). Pivoting of the entire leg actuator, of which there may be two, is driven by a similar element indicated at revolute joint 104 and as discussed elsewhere. In the embodiments, the revolute joint may include a drive as well. As discussed this joint may be moved laterally by a linear drive attached to or integrated in the prismatic joint 116.

Figure 12:
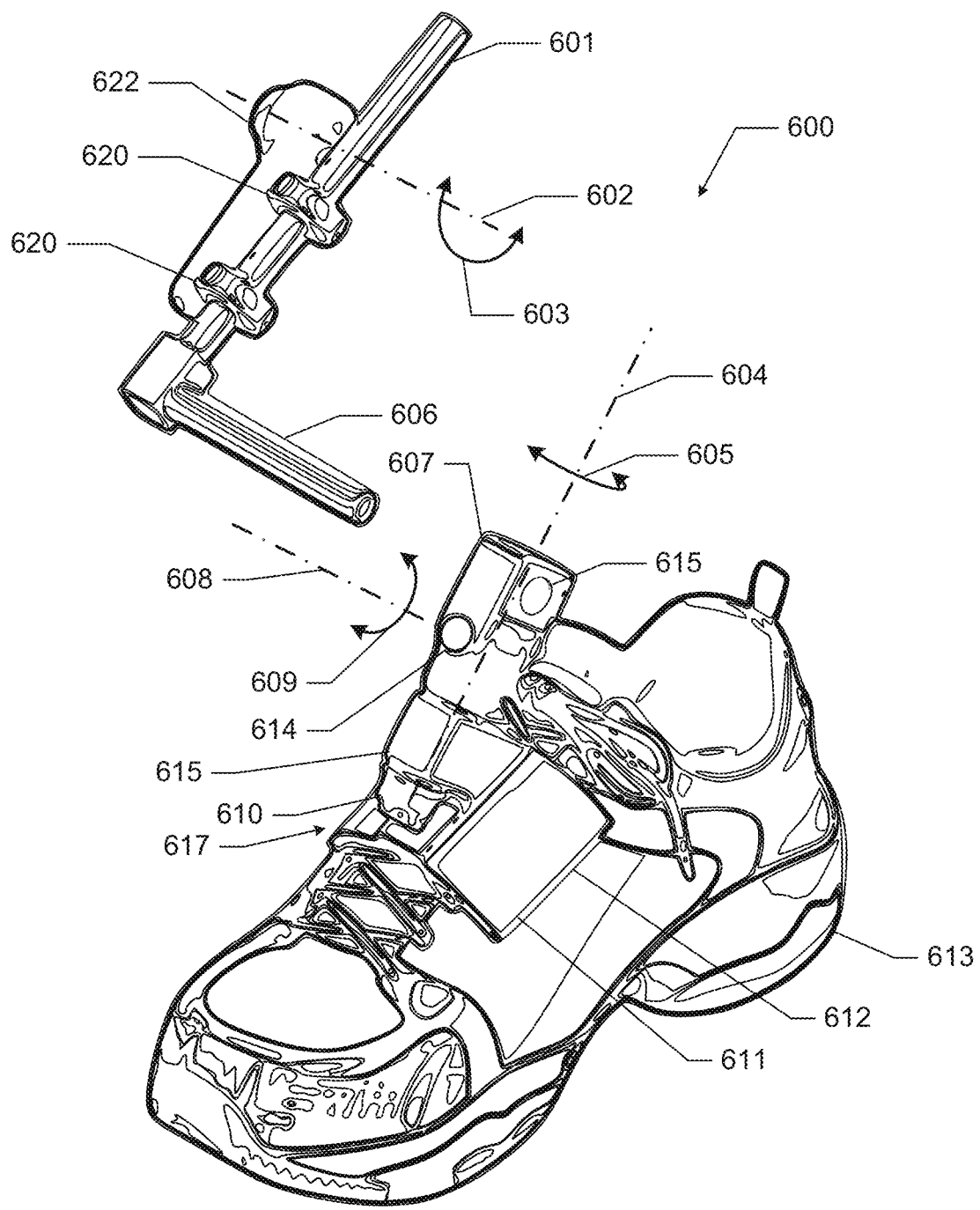
FIG. 12 shows a foot actuator that actively applies forces in the plantar/dorsiflexion mode while passively accommodating inversion/eversion of the foot, according to embodiments of the disclosed subject matter.

FIG. 12 shows a foot actuator ankle adapter 600 that actively applies forces in the plantar/dorsiflexion mode while passively accommodating inversion/eversion of the foot. This foot actuator ankle adapter 600 represents an optional component that may be used with any of the embodiments in place of the ankle adapter 322. As in ankle adapter 322, plantar/dorsiflexion rotation indicated by arrow 603 about an axis 602 is selectively urged, forced, or permitted by the active ankle revolute joint 326 which rotates arm 601 about the axis 602. A threaded rod 606 fixedly supports a bracket 607 that carries a revolute joint 614 that permits rotation of a shaft 615 about the axis of threaded rod 606 between and in the same plane as a vertical line and a line parallel to the aligned with the long axis of the foot. A member 615 carries a foot adapter 612 with hook-and-loop faster pads 611 for attachment of a belt that can run around and below the shoe 613 and attach at the opposite side 617 to secure the shoe 613 thereto. Member 615 is secured to a shaft that is supported by the revolute joint 614 and permits rotation of the foot adapter 612 about the axis 604 as indicated by arrows 605. Threaded rod 606 may pass through hole 615 and be secured by nuts (not shown) on either side of the bracket 607. It will be evident that the kinematic chain can force or resist plantar/dorsiflexion and permit inversion/eversion of the foot. Alternative kinematic mechanisms may also be provided, for example, a single R joint whose axis is parallel with the long axis of the foot may be used in an alternative embodiment. Note also that arm 601 can be positioned and secured at adjustable points therealong by friction fit fasteners indicated at 620 supported on arm 622 which is attached to the ankle revolute joint 326 driven by the embodiment of FIG. 4 and other embodiments. One or more additional joints may be added, according to known principles, to permit toe-in/toe-out motion of the ankle. Any of the passive motions of the ankle adapter 600 and the variants indicated may provide a degree of spring resistance to urge the foot into a particular preferred orientation. This feature may be provided by compliance in the links or by adjustable spring stops with a free-play range and progressive stop at the limits.

Figure 5:
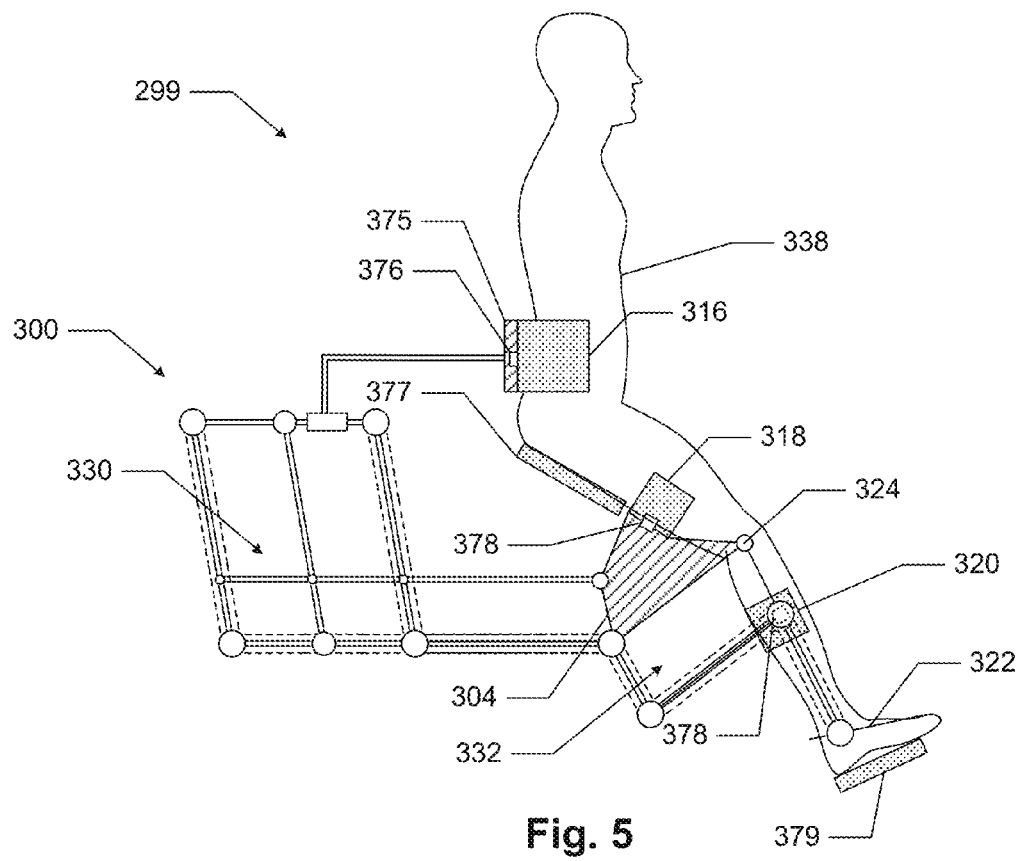
FIG. 5 shows the device of FIG. 4 in a receiving mode, according to embodiments of the disclosed subject matter.
Figures 6A, 6B:
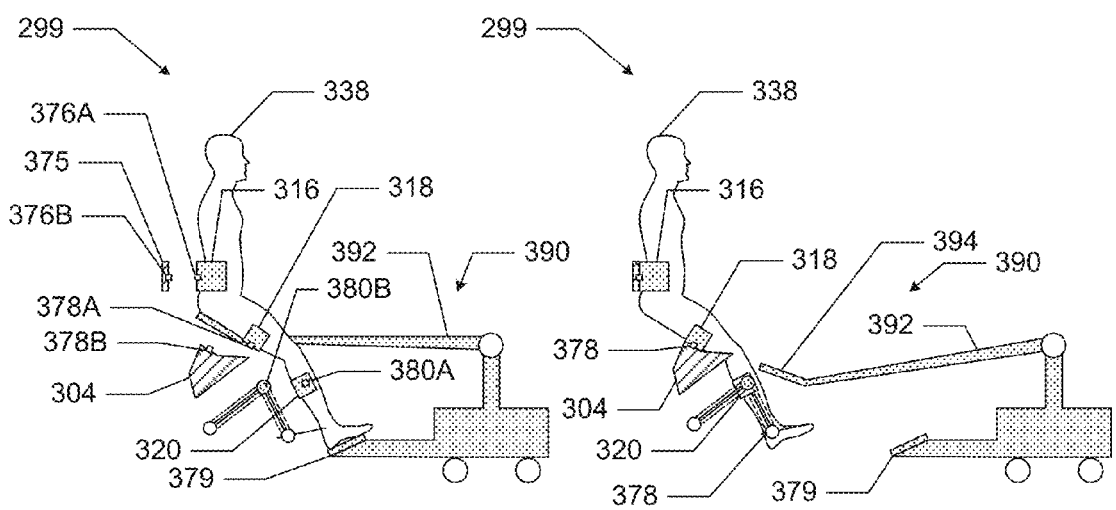
FIGS. 6A and 6B show a lift device that may assist patients with being adapted to the device of FIG. 5, according to embodiments of the disclosed subject matter.

Referring to FIGS. 5, 6A, and 6B, the movement training apparatus 299 of FIG. 4 may be provided with further features including quick connectors to allow patients to connect to at least some of the adapters (hip 316, thigh 318, knee 320, and ankle 322) in advance of connecting the patient 338 to the movement training apparatus 299. A system may incorporate a patient transport device as indicated at 390 in combination with the quick connectors or alone. Further, the system may include a special selectable configuration of the leg actuators 300 of the movement training apparatus 299 which selectable configuration facilitates rapid and comfortable loading of a new patient. In a method, new patients are strapped to the adapters, including one or more of the hip 316, thigh 318, knee 320, and ankle 322 adapters prior to being connected to the movement training apparatus 299. The adapters each may be provided with a connector that forms an interference or friction lock with the movement training apparatus 299 through the force and/or torque sensor. The pelvic adapter 316 may have complementary connector parts 376A and 376B, the latter being attached to a support 375 which may incorporate the aforementioned force-torque sensor for the hip. The thigh adapter 318 may have complementary connector parts 376A and 376B, the latter being attached to rigid element 304 which may incorporate the aforementioned force-torque sensor for the thigh. The shank adapter 320 may have complementary connector parts 380A and 380B, the latter being attached to a link of the knee parallelogram mechanism 332 which may incorporate the aforementioned force-torque sensor for the shank. Examples of suitable connector types include locking pins, locking key, grenade pin lock, screw fastener, screw clamp, quick-connector clamp, snap-release connector, strap, or any other type of releasable connector.

A transport device 390 has a seat 394 on the end of a boom 392. The transport device 390 has a foot stop 379 that may provide support if the seat is angled or to position the shank of the patient 338 for more convenient fitting of the hip 316, thigh 318, knee 320, and ankle 322 adapters. In FIG. 6A, a patient 338 is shown seated in the transport device 390. In a variant, the transport device could be fitted with a harness to support the patient 338 from above. In the illustrated embodiment, the seat 394 can be elevated or dropped by motorized boom 392. The seat is shown in a dropped position in FIG. 6B and elevated in FIG. 6A.

In embodiments, the movement training apparatus 299 is placed in a special configuration to receive a patient. In particular variants of the embodiments, the configuration employs one or more of the DOFs of the movement training apparatus 299 employed for rehabilitation of the patient, for example, here, the knee parallelogram mechanism 332 is drawn back to a position corresponding to a bent knee. In variants, the control response is adapted for transitioning the patient from detachment to attachment to the movement training apparatus 299. The control response for transition may be one in which the movement training apparatus 299 assumes a fixed position and then transitions to rehabilitation mode after attachment.

Note that the use of separate adapters that lock to the movement training apparatus 299 may be employed with different transport devices such as a hanging harness rather than a wheeled lift such as transport device 390. Note that FIGS. 5, 6A and 6B show only portions of the movement training apparatus 299 for clarity but the rest of the elements of movement training apparatus movement training apparatus 299 are assumed to be present.

Figure 8:
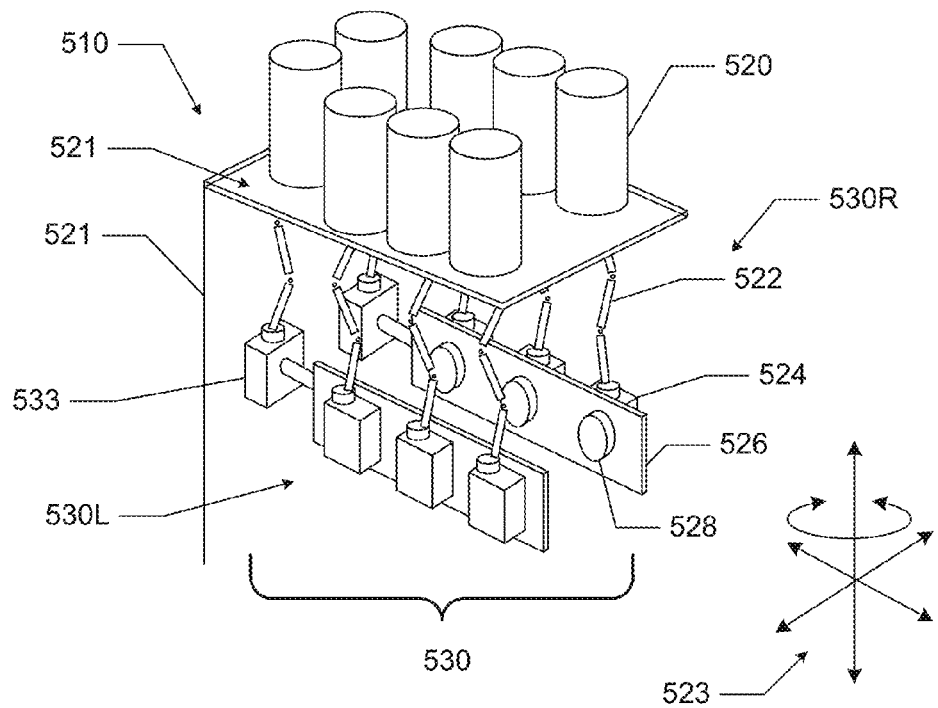
FIG. 8 shows a feature of embodiments in which the weight of motors is borne by a fixed stage to remove the inertia from the linkages that are directly connected to the patient, according to embodiments of the disclosed subject matter.

In embodiments, the transfer of motive force from the motor drives can accomplished with the use of cable drives or multi-link drive shafts such as constant velocity coupling (e.g., Rzeppa six-ball CV joint or simple universal joint), Thompson coupling, helical (beam) coupling, bellows coupling, Cardan joint (double Cardan joint), or similar flexible couplings. Further embodiments could employ multi-link belt drives as employed by motor-driven slow-speed dental drills (e.g., U.S. Pat. No. 2,917,828 to Page, hereby incorporated by reference herein). This may allow the gearing for such drives to be located on a fixed platform behind or otherwise remote from the patient. It may also permit the moving parts of the movement training apparatus 299 that follow the patient movements to have minimum inertial and frictional resistance. FIG. 8 shows a mechanism 510 that may be used with embodiments in which the weight of motors is borne by a fixed stage to remove the inertia from the linkages that are directly connected to the patient, according to embodiments of the disclosed subject matter.

Motor drives 520 may include reduction gearing or other transmission elements. The motor drives 520 may be connected through flexible couplings 522, such as the types identified above, including cable and multilink-type couplings. Zero backlash-type joints may be used. The motor drives may be supported on a fixed support indicated figuratively at 521. The hip and leg actuators making up a movement training apparatus (e.g., see 299) may move in any DOF including the fore-aft, lateral, vertical, and yaw directions indicated at 523 and associated with the motions provided by the trolley platform 102, described above. The flexible couplings 522 may apply torque through the flexible couplings 522 to each respective pulley of the timing belt system described above, through a right angle drive 524 or 533 (typ.). A primary pulley of the latter is indicated at 528. A direct drive of the hip adduction/abduction is indicated at 533. Eight motor drives 520 are shown and these may correspond to those for the four leg actuators for each leg 530L and 530K (both legs collectively indicated at 530— note that depending elements such as the knee parallelogram are not shown for clarity) comprising adduction/abduction, hip and knee flexion/extension, and ankle plantar/dorsiflexion. It is noted that the locating of the motor drives remotely as described with reference to FIG. 8 may be applied to other types of mechanisms than the embodiments specifically herein described.

Note that the embodiment of FIG. 8 defines a combination of features that facilitate control, including the mechanisms have a low moving mass, reducing the degree to which inertia must be compensated through control. Further, motions of the moving elements downstream of the drives which carry all of the moving mass downstream of the motor drive 522 gear reduction move in paths that are approximately the same as the limbs of the patient such that inertia of the elements is not amplified. Effectively, the linkages mechanically mimic or follow the magnitude and paths of the limbs. Combined with the light weight of these elements, control to provide a sensation of freedom of movement of the patient may be generated in cases where desirable.

Figure 11A:
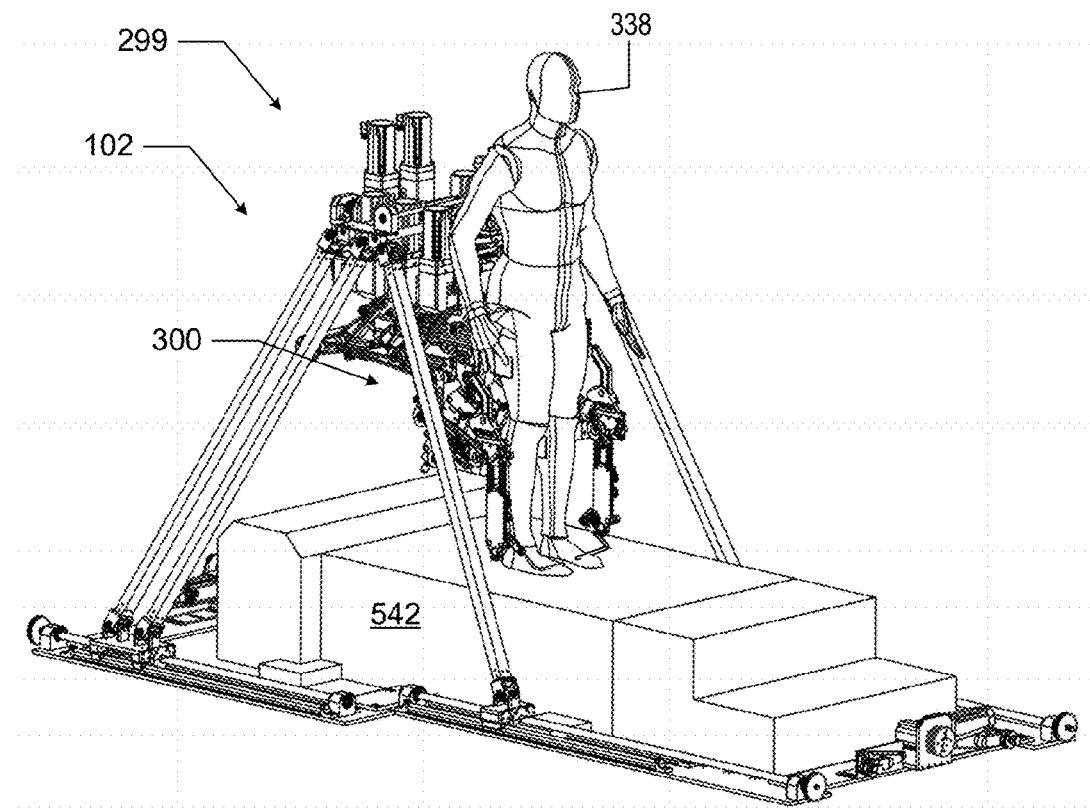
FIG. 11A shows a 3D model rendering of an embodiment of a movement training apparatus, according to embodiments of the disclosed subject matter.
Figure 11B:
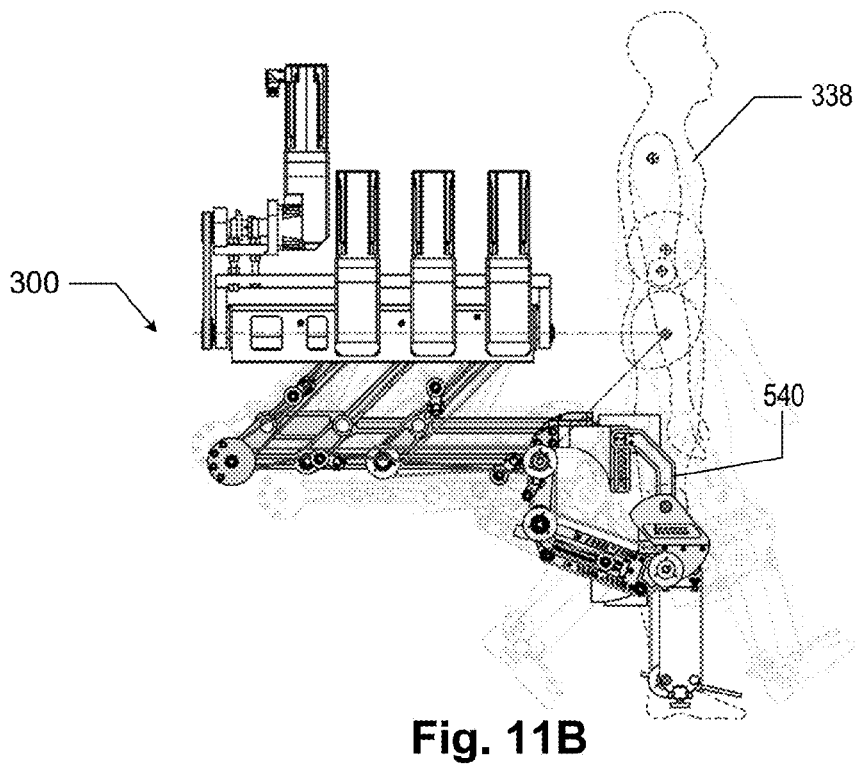
FIG. 11B shows a side view line drawing of a leg and hip actuator, according to embodiments of the disclosed subject matter.

FIG. 11A shows a 3D model rendering of an embodiment of a movement training apparatus, according to embodiments of the disclosed subject matter. FIG. 11B shows a side view line drawing of a leg and hip actuator according to embodiments of the disclosed subject matter. It may be noted that the placement of the leg actuators is such that they are out of view of the patient and also positioned behind the patient and low and to the side out of the path of hand swings, except for a thin rigid link astride the knee and indicated at 540. A treadmill 542 may be used as shown with any of the embodiments.

Figure 7A:
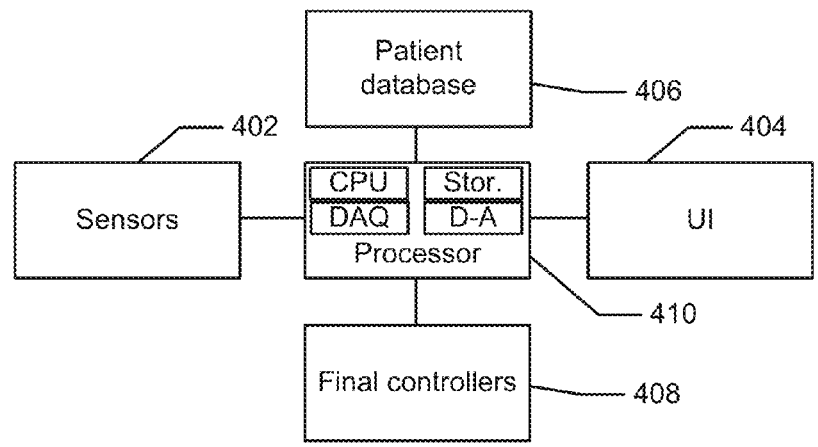
FIGS. 7A and 7B show physical and conceptual elements, respectively, of a control system that may be used with any of the embodiments.
Figure 7B:
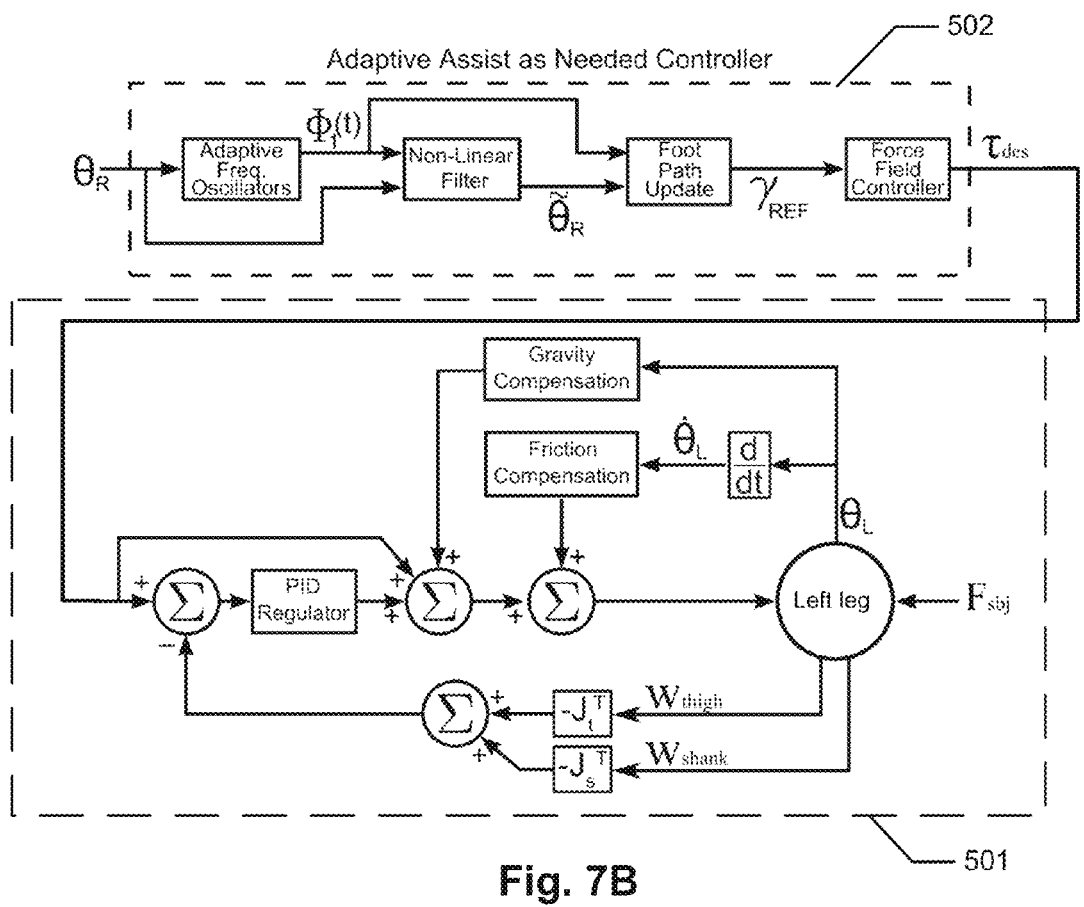

Referring now to FIGS. 7A and 7B, a controller 410 for the movement training apparatus 299 is the same for the leg actuators 300 and the trolley platform 102. The controller 410 has a processor 410 with data storage that may include non-volatile data storage and random access memory elements (Stor.). Further it may have a data acquisition portion (DAQ) that interfaces to sensors for receiving signals from the various sensors of the described embodiments. It may have output components such as audio and video adapters as well as input interfaces to support interaction with one or more user interface (UI) elements 404. It may have a digital to analog converters (D-A) for output signals to final controllers 408 that drive motors. It may have a processing unit (CPU) for numerical computation and execution of programmatic instructions. Apart from the data storage, it may be connected to data sources including databases, for example a patient database 406 with patient profiles such as the patient's particular limb lengths, diameters, strength and weakness parameters, etc. that are useful for fitting and controlling rehabilitation using the movement training apparatus 299.

The controller 410 includes a portion 501 employing force-feedback loops with gravity and friction compensation terms 501 with a portion providing adaptive assist as needed (AAN) control. Instead of controlling actuator torque output (traditional torque control), the interaction error may be controlled using force-torque sensors mounted between each adapter (which may include an orthosis) and the user's body (direct force control) to cancel out at least a fraction of undesired interaction forces arising from the inertia of the actuator links, without the use of inertial compensators. In embodiments, inertial compensation may be used in addition or alternatively.

The AAN controller 502 facilitates recovery of gait symmetry. The controller integrates a static non-linear force tunnel associated with a target footpath, with adaptive function provided through the combination of adaptive oscillators (AFO) and kernel-based nonlinear filters. The AFO extracts a phase of the gait. Non-linear filters learn trajectories of the hip and knee joints of the unimpaired leg as a function of the phase. The corresponding data is stored in profiles for respective patients. These profile data are then used update a reference footpath continuously to shape the behavior of the assistive force field acting on the contralateral leg (see AAN controller 502). A treatment log may be stored in the profile data after each session which may include force-torque sensor data, footpath error, and other data related to each treatment effective to reveal patient progress. Further data stored in the patient log may be used to update control parameters specific to each patient, to each class of patient, and to all patients.

Joint angle trajectory $\theta(t)$ during walking may be approximated by a periodic non-sinusoidal signal, whose frequency spectrum comprises only multiples of a fundamental frequency. A suitable estimator $\hat{\theta}(t)$ may be represented as a sum of M oscillators:

$$\theta(t) = \theta_0 + \Sigma_1^M a_i \sin(\phi_i(t)), \quad (1)$$

where the i-th oscillator tracks the i-th harmonic component, similarly to a real-time Fourier decomposition. The phase of the fundamental harmonic, namely $\phi_1(t)$, may be used to estimate the gait phase. The set of equations governing how the pool of oscillators learns the frequency of the teaching signal $F(t) = \theta(t) - \hat{\theta}(t)$ may be represented by:

$$\dot{\phi}_i(t) = i\omega + \epsilon F(t)\cos(\phi_i(t)), \, i=1,\ldots,M$$

$$\dot{\omega}(t) = \epsilon F(t)\cos(\omega_1(t)),$$

$$\dot{a}_i(t) = \nu F(t)\sin(\phi_i(t)), \, i=1,\ldots,M$$

$$\dot{\theta}_0(t) = \nu F(t), \quad (2)$$

where $\phi_i$, (i $\omega$) are the phase and frequency of the i-th oscillator, and $\epsilon$, $\nu$ are the coupling strength and the learning factor of the AFO. Subsequently, based on the estimate $\phi_1(t)$, N equally spaced kernel functions in the form $$\Psi_i(\varphi_1(t)) = \exp\left[h\left(\cos\left(\varphi_1(t) - \frac{2\pi i}{N}\right) - 1\right)\right]$$

may be used to reconstruct the signal $\theta(t)$:

$$\tilde{\theta}(t) = \frac{\sum_1^N \Psi_i(\varphi_1(t))w_i(t)}{\sum_1^N w_i(\varphi_1(t))} \quad (3)$$

Here, $\tilde{\theta}(t)$ is the reconstructed signal and h defines the width of the kernel functions. Incremental learning of weights $w_i$ is achieved at each time sample n through a RLS method with forgetting factor $\lambda$:

$$w_i(n+1) = w_i(n) + \Psi_i(n)P_i(n+1)e_r(n),$$
$$e_r(n) = [\theta(n) - w_i(n)],$$

$$P_i(n+1) = \frac{1}{\lambda}\left(P_i(n) - \frac{P_i(n)^2}{\frac{\lambda}{\Psi_i(\varphi_1(n))} + P_i(n)}\right) \quad (4)$$

This algorithm runs in parallel for the hip and knee flexion/extension angles of the unimpaired leg—as measured by the encoders embedded in the movement training apparatus 299—yielding the estimates $\tilde{\theta}_{HIP}(t)$ and $\tilde{\theta}_{KNEE}(t)$. The parameter $\lambda$ controls speed with which these estimates adapt to variations of the patient or trainer's gait. If $\lambda=1$, the same relative emphasis is given to recent and older data, and therefore the algorithm adapts slowly. Conversely, when $\lambda<1$, more emphasis is given to recent data, and the estimates adapt quickly.

Let $\gamma_{REF}(\phi)$ be the target footpath for the impaired leg:

$$\gamma_{REF}(\phi) = (x(\phi), y(\phi)), \, \phi \in [0; 2\pi), \quad (5)$$

then the most recent angle estimates, together with the information on the current phase, can be used to locally update the target footpath:

$$\gamma_{REF}(\phi(t)) = f(\theta_{HIP}(t), \theta_{KNEE}(t)) \quad (6)$$

where $f$ is the (forward kinematics) function mapping subject's hip and knee angles to the position of his/her foot in the sagittal plane. In Eqn. (6), $\phi(t)$ can be equivalently chosen as $\phi_{1,HIP}(t)$ or $\phi_{1,KNEE}(t)$. The assistive force to be exerted on the wearer's impaired foot depends on the position of the latter relative to $\gamma_{REF}$. The force-field behavior is modeled by a nonlinear virtual spring that exerts a normal force towards the prescribed footpath if the deviation of the subject's foot from $\gamma_{REF}$ exceeds an adjustable threshold:

$$F = \begin{cases} k_N(d - D_0)^2 n & \text{if}(d > D_0), \\ 0n & \text{otherwise}, \end{cases} \quad (7)$$

where $k_N$ is the stiffness of the virtual spring, $D_0$ is the width of the force tunnel, d is the distance of the subject's foot from $\gamma_{REF}$ and n is the unit vector directed along the line connecting the subject's ankle point to the closest point of $\gamma_{REF}$. F is finally mapped to the vector of equivalent interaction torques $\tau_{des}$ which is fed to the low-level controller (FIG. 2).

Figure 9:
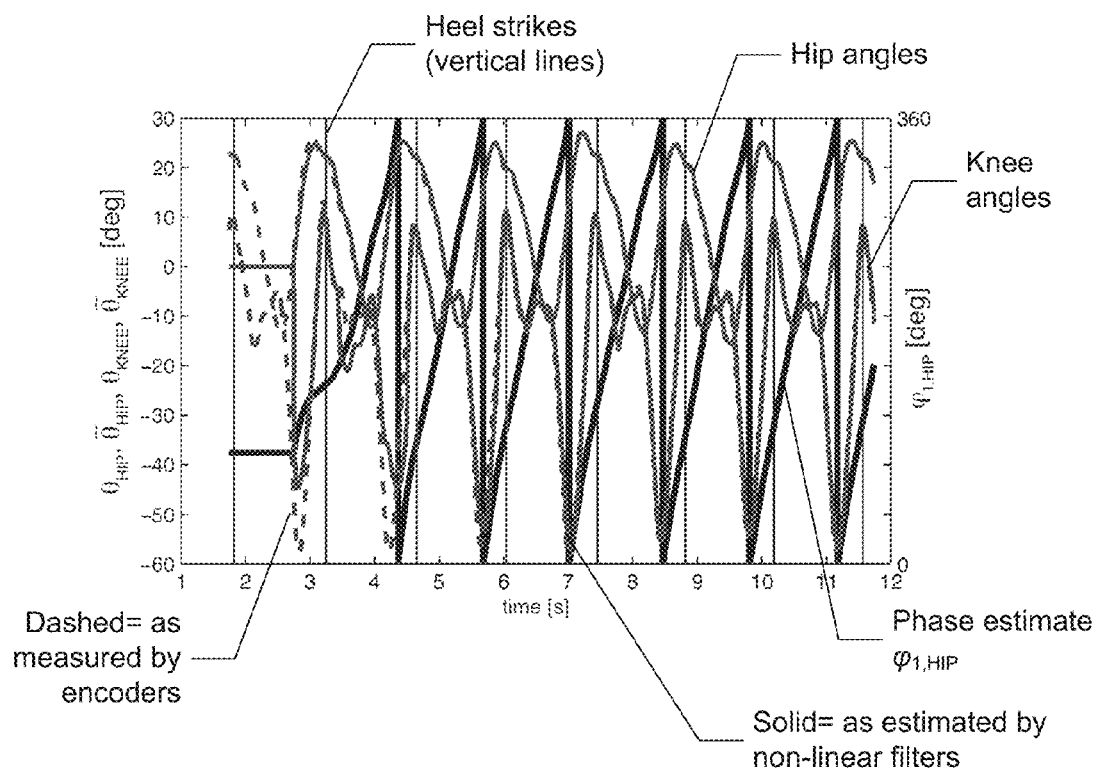
FIG. 9 shows hip and knee angles of the right leg as measured by encoders and estimated by non-linear filters as well as heel strikes and phase estimate during experiments with an embodiment of a movement training apparatus, according to embodiments of the disclosed subject matter.

In the controller 410, AFO, nonlinear filters and footpath update may run at 500 Hz, whereas the force-field controller may run at 1 kHz. Preliminary tests showed that M=6 oscillators with $\nu$=0.5 and $\epsilon$=12 reach synchronization in about 3 steps. In specific embodiments, N=90 was found to provide an optimal tradeoff between accuracy of estimation and computational load, and the width of kernel functions was set to h=2.5 N. The forgetting factor $\lambda$=0.995 was chosen experimentally to provide smooth adaptation of the reference footpath. FIG. 9 shows how $\phi_{1,HIP}(t)$ and the estimates $\tilde{\theta}_{HIP}(t)$ and $\tilde{\theta}_{KNEE}(t)$ evolved with time, after the AFO was activated, at t=2.7 s, while a trainer was walking in the movement training apparatus 299 at 0.9 m/s. As can be seen by the convergence of the dashed curves and solid curves, the AFO progressively synchronizes to the gait cycle and the nonlinear filters (anchored to the phase estimate) learn the input signals, such that estimation errors become negligible after five steps. The control scheme permits the target footpath to adapt progressively as the walking speed is changed, for example from 1.0 to 0.5 m/s.

In alternative embodiments, gait symmetry may be assisted by directly feeding the trajectory of the unimpaired foot to reshape the force field. This approach may reduce gait stability in case of variations of the gait pattern induced, for instance, by changes of walking cadence. The update of the reference template would necessarily be done all at once at discrete gait events (e.g., at initial contact of one foot). With the approach proposed above, however, the target footpath adapts smoothly to changes in frequency and shape. The online estimation of the gait phase by means of the AFO allows for continuous update of the reference trajectory, while the action of non-linear filters with forgetting factor smoothens the transitions in gait footpath, thus preventing abrupt changes. The patient or trainer is never constrained to follow a fixed trajectory and assistive forces are nil if his/her foot is sufficiently close to the reference footpath.

In tests, to approximate an asymmetric gait impairment, for example as associated with hemiparesis, additional weights (2.3 kg) were attached to a subject's left distal shank. Location and magnitude of the load were chosen to alter gait kinematics significantly. A five-minute familiarization session was included prior to the experiment to let the subject acclimate to walking in the exoskeleton. Afterwards, subjects walked in the movement training apparatus 299 under four different conditions, each one lasting two minutes, while a treadmill speed was set to 0.9 m/s. During the experiments, pelvis rotation and lateral motion were locked in the movement training apparatus 299, and the subject's ankle was not connected to the exoskeleton, to allow fitting of the ankle weight.

A first session (baseline) included treadmill walking while the movement training apparatus 299 was controlled in zero-interaction mode where the desired interaction torques reflected at the hip and knee joints of each leg were set to zero, as were the desired interaction forces at the pelvic adapter. The first session was used to assess the subject's level of gait symmetry at baseline. In a second session (weight), the task was similar except for the addition of the ankle weight. It was observed that healthy subjects required approximately fifty strides to reach steady-state joint patterns after the addition of external weights. The deadaptation process was found to be slower, taking up to seventy strides. To guarantee a complete wash-out before testing the controller, a deadaptation session was included that resembled the baseline. A third session (force field) involved testing the effects of the adaptive force field on the subject walking with the weights. Besides haptic guidance, in this subjects were also given augmented visual feedback on the target footpath and on the current position of their foot.

Data collected by the movement training apparatus in the last sixty seconds of each session were sampled at 500 Hz and processed. Stride-to-stride subdivision was achieved by means of footswitches. In the following, results are presented from two representative symmetry metrics, the normalized error area (NEA) and the double-support ratio (DS ratio), which address spatial and temporal asymmetry, respectively. The former was defined as the deviation area between two successive left and right footpaths, divided by the area of the reference footpath (right leg footpath). t-tests were run on each subject separately, to check for significant differences in the two metrics across the four sessions ($\alpha$=0.05). Bonferroni correction was used to control the familywise error rate.

Figure 10A:
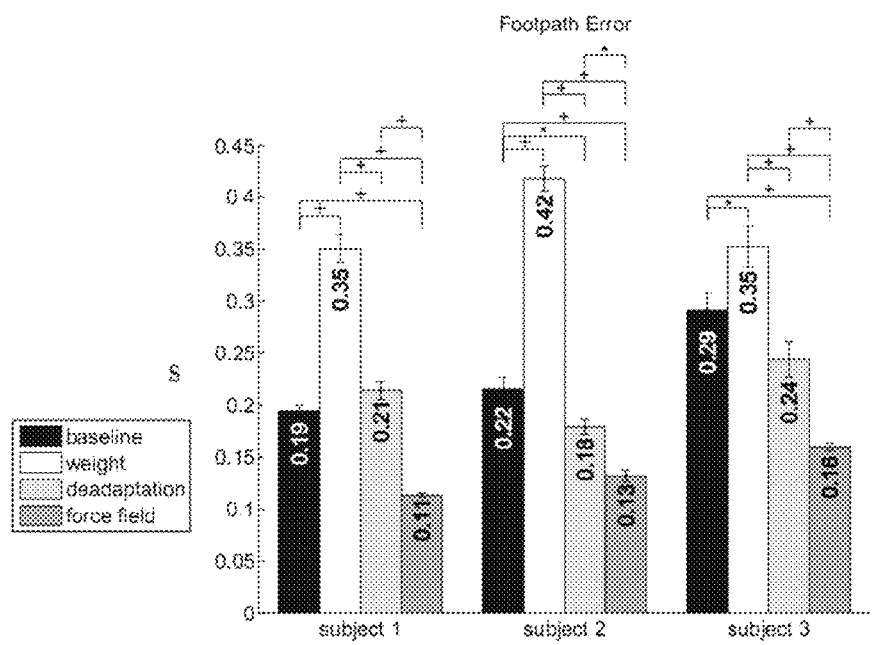
FIGS. 10A and 10B show error graphs associated with experiments with an embodiment of a movement training apparatus, according to embodiments of the disclosed subject matter.
Figure 10B:
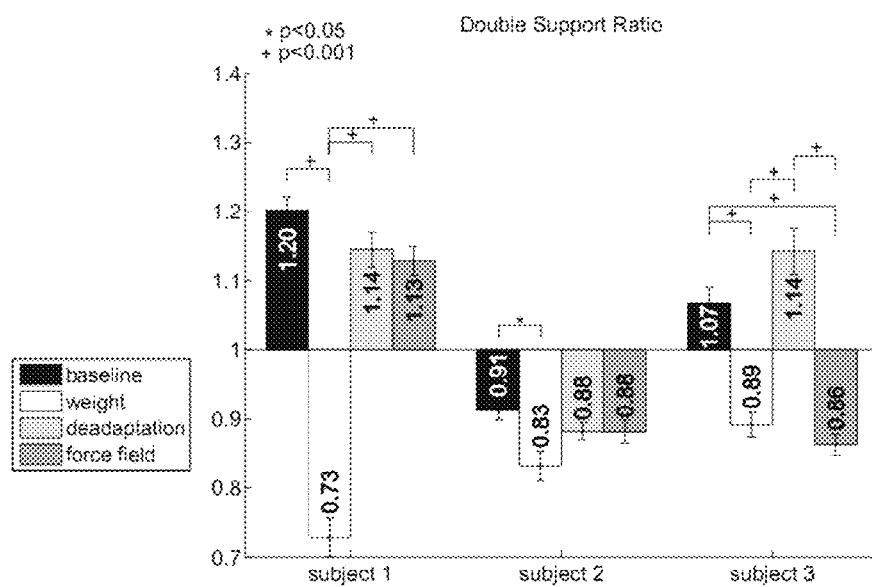

FIGS. 10A and 10B show that for all the subjects, the addition of the ankle weight significantly increased the deviation area between the left and right footpaths compared to baseline (p<0.001). A baseline value was successfully recovered during deadaptation. All three subjects were able to improve gait symmetry when walking with the adaptive controller, with the deviation area being significantly smaller than in the weight session (p<0.001). The deviation area was found actually to be smaller than in the baseline session for all the subjects (p<0.001). This indicates a benefit of combined haptic guidance provided by the movement training apparatus 299 with visual feedback, which may augment accurate volitional control of the foot trajectory.

A type of asymmetry may be defined according to a double support ratio, which is the ratio of double support (DS, a phase in the walking cycle) of the right leg and that of left leg. During double support, the weight is progressively transferred to either the left leg (right DS) or to the right leg (left DS). A DS ratio less than unity, then, indicates decreased time available to shift the load to the left leg. This change was significant in all three subjects, when comparing the weight session to baseline (p<0.001, FIG. 7). A known effect of asymmetric weighting is increased swing time in weighted limb due to the extra mass. This was reflected in all subjects by a decrease in the ratio of the stance periods of right and left legs. A prolonged swing period in the left leg, in turn, delays the initial contact of the left foot, thus reducing the right DS. During the deadaptation session, this deviation was recovered by all subjects (p>0.05). The adaptive force field helped subject 1 and 2 recover temporal symmetry, their DS ratio in session force field being not significantly different from the baseline value. This was not the case of a particular subject—subject 3—(p=0.004), whose DS ratio during the last session was actually close to the non-assisted weighted condition (p>0.05).

The force-field proved to be more effective in restoring spatial symmetry than temporal symmetry, at least for one subject. A possible explanation is that the force field prescribed a target footpath rather than a target trajectory, thus allowing subjects to adjust the actual timing of movement. Spatial and temporal variables were found to be linked by the constraint on the walking speed (imposed by the treadmill), and indicates the beneficial effects on temporal symmetry detected in subject 1 and 2.

According to embodiments, a controller continuously modulates the force field applied to an impaired leg based on the outputs of kernel-based non-linear filters that learn the movements of an unimpaired leg. The controller thereby smoothly accommodates changes in gait pattern and timing, such as those derived from modifying the walking speed. Experimental results showed that the controller was effective in helping three healthy subjects improve gait symmetry, after their gait pattern was temporarily altered by ankle weighs. Spatial symmetry was recovered more easily than temporal symmetry. The controller improved subjects' spatial symmetry even beyond the baseline values: given the AAN nature of the force controller, this effect appears to be due to the visual feedback (active during the force field session) favoring accurate volitional control of the foot trajectory, rather than to only the assistance of the movement training apparatus 299.

Known systems provide body weight support and move the hip and knee joints of both legs through a predefined path, but do not provide active ankle or assistance to motion in the parasagittal plane for the leg. They are further limited in that they only provide superior/inferior motion to the pelvis. Another known system provides three active DOFs per leg, flexion/extension of the hip and knee, and hip abduction/adduction; two active DOFs at the pelvis, anterior/posterior, and lateral motion; and passive superior/inferior motion at the pelvis. It uses prismatic joints to provide the controlled pelvic motion. The motors for the legs are remotely located through the use of Bowden cables.

The disclosed embodiments include a unilateral device which provides controlled hip and knee flexion/extension, and passive abduction/adduction. It has four passive DOFs provided to the pelvis, three translational and rotation about the vertical axis. Other embodiments provide four active DOFs at the pelvis. The structure that provides this motion is a closed chain parallel mechanism. The legs provide active flexion/extension at the hip, knee, and ankle; as well as hip abduction/adduction. The motors for the embodiments are remotely located at the pelvis to reduce the inertia of the leg. This is accomplished using parallel linkages to create virtual joint centers at the hip, and a series of belt driven joints for the knee and ankle.

The disclosed subject matter may provide a versatile system to test and implement control strategies, mechanical design, and motor learning strategies and theories. The amount of motion provided to the person can be limited or allowed to determine the optimal design to gain the best rehabilitative care. It is also capable of providing perturbation forces to test/train recovery strategies. The ability to train and correct abnormal ankle use may have a desirable effect on recovery of a more natural gait pattern in impaired individuals. The disclosed subject matter could potentially be used in research centers to gain an understanding of the motor control system. It could also be using in physical rehabilitation clinics to help patients recovering from disabilities caused by injury such as stroke or neurological trauma or disease.

It will be appreciated that the modules, processes, systems, and sections described above can be implemented in hardware, hardware programmed by software, software instruction stored on a non-transitory computer readable medium or a combination of the above. For example, a method for robotically-assisted movement rehabilitation can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, active movement training devices, methods, and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicant intends to embrace all such alternatives, modifications, equivalents, and variations that are within the spirit and scope of the present invention.

The invention claimed is:

1. A rehabilitation machine, comprising:
   a chassis with actuators positioned behind a patient area;
   the actuators having supports projecting toward the patient area and having respective adapters shaped to engage the legs of a patient at the thigh, the calf, and the foot while the patient is in a standing or walking posture;
   the actuators having motors, transition elements, and linkages connected to apply moments through said adapters to achieve, for each leg, hip adduction/abduction, hip flexion/extension, knee flexion/extension, and foot plantar flexion/dorsiflexion according to signals from a controller;
   the actuators being confined to a space, largely behind the patient, such that free arm swing is permitted when the patient is attached.

2. The machine of claim 1, further comprising a pelvic adapter projecting forward and shaped and positioned to receive the hips of a patient.

3. The machine of claim 2, wherein the actuators are supported on a movable subframe.

4. The machine of claim 2, wherein the pelvic adapter is movably supported to permit movement thereof in a confined range including lateral pelvic translation.

5. The machine of claim 2, wherein the pelvic adapter is movably supported to permit movement thereof in a confined range including lateral pelvic rotation.

6. The machine of claim 2, wherein the pelvic adapter is movably supported to permit movement thereof in a confined range including lateral pelvic translation and pelvic rotation.

7. The machine of claim 2, wherein the pelvic adapter is movably supported to permit movement thereof in a confined range including vertical pelvic translation.

8. The machine of claim 2, wherein the pelvic adapter is movably supported to permit movement thereof in a confined range including lateral pelvic rotation and vertical translation.

9. The machine of claim 2, wherein the pelvic adapter is movably supported to permit movement thereof in a confined range including vertical pelvic translation and pelvic rotation.

10. The machine of claim 2, wherein the pelvic adapter is movably supported to permit movement thereof in a confined range including motion of the pelvis through all six of translation and rotation axes.

11. The machine of claim 1, wherein the actuators include a subchassis carrying motors and first transmission elements movably mounted to the subchassis.

12. The machine of claim 1, wherein the chassis includes an open frame to accommodate a treadmill thereunder.

13. The machine of claim 12, wherein the actuators include a subchassis carrying motors and first transmission elements movably mounted to the frame and a parallelogram linkage that carries the thigh adapter.

14. The rehabilitation machine according to claim 1, wherein
   the actuators are entirely outside of reach of the patient's arms when the patient is attached to the respective adapters of the supports in a normal walking position.

15. The rehabilitation machine according to claim 1, wherein
   the actuators are configured to project a kinematic equivalent of a patient's legs from joints located behind the patient to the adapters, such that all the joints of the kinematic mechanism corresponding to at least the hip are located remote from and behind the patient, and out of the range of a normal walking swing of the connected patient's arms.

16. A rehabilitation machine, comprising:
   a chassis with actuators positioned behind a patient area;
   the actuators having supports projecting toward the patient area and having respective adapters shaped to engage the legs of a patient at the thigh, the calf, and the foot while the patient is in a standing or walking posture;
   the actuators having motors, transition elements, and linkages connected to apply moments through said adapters to achieve, for each leg, hip adduction/abduction, hip flexion/extension, knee flexion/extension, and foot plantar flexion/dorsiflexion according to signals from a controller;
   the actuators being at least partially confined to a space behind the patient, such that free arm swing is permitted when the patient is attached, wherein
   the chassis includes an open frame to accommodate a treadmill thereunder,
   the actuators include a subchassis carrying motors and first transmission elements movably mounted to the frame and a parallelogram linkage that carries the thigh adapter, and
   the parallelogram linkage carries second transmission elements that connect to the first transmission elements, the second transmission elements driving linkages depending from the parallelogram linkage with ranges of motion to apply moments to the calf adapter and the foot adapter.

17. The machine of claim 16, wherein the controller is configured to provide an assistive or resistive mode by driving the motors in such a way that a patient resisting or assisting programmed forces transmitted to the adapters may impede or advance the programmed motion of the adapters to a predefined degree.

18. The machine of claim 17, wherein the mechanical impedance forces required so as to impede or assist the forces transmitted to the adapters include the inertia of linkages and transmission elements but not the motors, the motors being carried by the subchassis.

19. A rehabilitation machine, comprising:
a chassis with actuators positioned behind a patient area;
the actuators having supports projecting toward the patient area and having respective adapters shaped to engage the legs of a patient at the thigh, the calf, and the foot while the patient is in a standing or walking posture;
the actuators having motors, transition elements, and linkages connected to apply moments through said adapters to achieve, for each leg, hip adduction/abduction, hip flexion/extension, knee flexion/extension, and foot plantar flexion/dorsiflexion according to signals from a controller;
the actuators being at least partially confined to a space behind the patient, such that free arm swing is permitted when the patient is attached,
wherein the actuators include a subchassis that is linked to motors supported on a fixed frame, first transmission elements being movably mounted to the subchassis and motive forces conveyed from the motors through flexible transmission couplings.

20. The machine of claim 19, wherein the flexible transmission couplings include multiple zero-backlash links.

21. The machine of claim 19, wherein the flexible transmission couplings include constant velocity joints.

22. The machine of claim 19, wherein the first transmission elements include joints and links that kinematically mirror the movements of the hip and knee and are projected directly from behind.

23. The machine of claim 19, wherein the first transmission elements include timing belts and pulleys.

24. A rehabilitation machine, comprising:
a chassis with actuators positioned behind a patient area;
the actuators having supports projecting toward the patient area and having respective adapters shaped to engage the legs of a patient at the thigh, the calf, and the foot while the patient is in a standing or walking posture;
the actuators having motors, transition elements, and linkages connected to apply moments through said adapters to achieve, for each leg, hip adduction/abduction, hip flexion/extension, knee flexion/extension, and foot plantar flexion/dorsiflexion according to signals from a controller;
the actuators being confined to a space, largely behind the patient, such that free arm swing is permitted when the patient is attached,
wherein the actuators are configured to apply controlled forces to the pelvis, hip, knee and ankle joints simultaneously to control four degrees of freedom at the pelvis including vertical rotation, anterior/posterior, superior/inferior and lateral motions and four degrees of freedom at each leg including hip adduction/abduction, hip and knee flexion/extension, and ankle plantar/dorsiflexion.

25. A rehabilitation machine, comprising:
a chassis with actuators positioned behind a patient area;
the actuators having supports projecting toward the patient area and having respective adapters shaped to engage the legs of a patient at the thigh, the calf, and the foot while the patient is in a standing or walking posture;
the actuators applying moments through said adapters to each leg according to signals from a controller, wherein
the actuators, apart from the adapters, are confined to a space behind the patient, such that uninhibited normal arm swing is permitted when the patient is attached.

* * * * *